United States Patent [19]
Klingenbeck-Regn et al.

[11] Patent Number: 5,722,407
[45] Date of Patent: Mar. 3, 1998

[54] APPARATUS AND METHOD FOR EXAMINING TISSUE WITH LIGHT OF DIFFERENT WAVELENGTHS

[75] Inventors: Klaus Klingenbeck-Regn, Nueremberg; Arnulf Oppelt, Spardorf, both of Germany

[73] Assignee: Siemens Aktiengesellschaft, Munich, Germany

[21] Appl. No.: 665,352

[22] Filed: Jun. 17, 1996

Related U.S. Application Data

[63] Continuation of Ser. No. 298,173, Aug. 30, 1994, abandoned.

[30] Foreign Application Priority Data

Sep. 8, 1993 [DE] Germany .................. 43 30 460.5

[51] Int. Cl.$^6$ .................................................. A61B 5/05
[52] U.S. Cl. ..................... 128/653.1; 128/633; 128/665
[58] Field of Search .................................. 128/664, 665, 128/633, 653.1; 250/330, 332; 356/432–435

[56] References Cited

U.S. PATENT DOCUMENTS

| | | |
|---|---|---|
| 3,910,701 | 10/1975 | Henderson et al. . |
| 4,850,365 | 7/1989 | Rosenthal ................... 128/664 |
| 4,908,762 | 3/1990 | Suzuki et al. ................ 356/434 |
| 4,975,581 | 12/1990 | Robinson et al. . |
| 5,119,815 | 6/1992 | Chance ....................... 356/432 |
| 5,131,398 | 7/1992 | Alfano et al. . |
| 5,293,873 | 3/1994 | Fang ......................... 128/664 |
| 5,309,907 | 5/1994 | Fang et al. . |
| 5,337,745 | 8/1994 | Benaron ..................... 128/664 |
| 5,349,951 | 9/1994 | Ito et al. ................... 128/664 |
| 5,555,885 | 9/1996 | Chance ....................... 128/664 |

OTHER PUBLICATIONS

"Time–Dependent Optical Spectroscopy and Imaging for Biomedical Applications" Wilson et al., Proc. of the IEEE, vol. 80, No. 6, Jun., 1992, pp. 918–930.

Encyclopedia of Medical Devices and Instrumentation, vol. 3, Webster, Ed., p. 1841.

*Primary Examiner*—Brian L. Casler
*Attorney, Agent, or Firm*—Hill, Steadman & Simpson

[57] ABSTRACT

In an apparatus and method for examining tissue by transillumination of the tissue, light having different, defined wavelengths is emitted from a plurality of monochromatic light sources into tissue under examination, the light emerging from the tissue is detected by a detector arrangement for detecting the parts of the emitted light transmitted by the tissue, and signals from the detector arrangement are supplied to an evaluation unit. The evaluation unit calculates data with respect to the concentration of the different tissue components in the tissue under examination from the different signals on the basis of stored data that correspond to the light absorption of different tissue components.

14 Claims, 5 Drawing Sheets

APPARATUS AND METHOD FOR EXAMINING TISSUE WITH LIGHT OF DIFFERENT WAVELENGTHS

This is a continuation of application Ser. No. 08/298,173 filed Aug. 30, 1994 now abandoned.

BACKGROUND OF THE INVENTION

1. Field of the Invention

The present invention is directed to an apparatus and method for examining tissue wherein the tissue is transilluminated with light and medical conclusions are drawn based on the interaction of the tissue with the light.

2. Description of the Prior Art

Known apparatuses of the above type can operate with visible, NIR or IR light. The wavelength of visible light lies between 380 and 780 nm, that of NIR light, i.e. of near-infrared light, lies between 780 nm and 1.5 µm and that of IR light, i.e. of infrared light, lies between 1.5 µm and 1 mm. The wavelength range from 600 nm through 1.2 µm is especially suitable for apparatuses of the type initially cited.

Many optical properties of tissue, for example the absorption, the scatter and the spectral properties, can be identified by irradiating the tissue with light. For example, it is possible to identify tissue modifications in mammadiagnostics from light emitted into the breast, the light emerging therefrom being detected and the information acquired in this way is suitably interpreted. Known apparatuses merely allow the presence of inhomogeneities in the examined tissue to be identified. Perceptions about the nature or characteristics in the examined tissue, particularly of a tissue inhomogeneity, cannot be derived from the measured results in known systems.

SUMMARY OF THE INVENTION

An object of the present invention is to provide an apparatus of the type initially described that allows information about the concentration of the tissue components that are present in the examined region to be obtained.

This object is inventively achieved in an apparatus for examining tissue with light having means for emitting light from a plurality of monochromatic light sources having respective defined, different wavelengths into the tissue to be examined substantially simultaneously through a light exit zone that is substantially the same for the light of each wavelength, means for detecting light after passing through the tissue, having a light entry zone disposed opposite the light exit zone and which produces output signals corresponding to the respective intensities in the detected light of the parts of the light having the defined, different wavelengths, and evaluation means to which the output signals are supplied, the evaluation means calculating data with respect to the concentration of different tissue components from the output signals on the basis of stored data that correspond to the absorption of a plurality of different tissue components for the light having the defined, different wavelengths. The number of different tissue components corresponds at most to the number of defined, different wavelengths. The object is also achieved in a corresponding method.

The means for detection thus detect the parts of the light emitted into the tissue under examination from the means for irradiation that are transmitted by the tissue and generate signals for the defined, different wavelengths that correspond to the intensity of the parts of the light transmitted by the tissue under examination, and using these signals the evaluation means calculate data corresponding to the concentration of the different tissue components in the tissue. As a consequence of the use of stored data related to the absorption of different tissue components for the light of the wavelengths employed in the examination of the signals supplied by the means for detection, the apparatus of the invention thus allows statements to be made about the concentration, preferably the relative concentration, of tissue components in the tissue region under examination. The data corresponding to the absorption of the different tissue components need not be data that identify the absorption itself. Instead, the data can indicate the transmission or the transparency or extinction or the extinction coefficient of the tissue components for the defined, different wavelengths.

According to an embodiment of the invention, the evaluation means calculate the relative concentration of the different tissue components using the equation $$A(\lambda_i) = -\log\frac{I(\lambda_i)}{I_o(\lambda_i)} = d \cdot \sum_{v=1}^{L} \alpha_v(\lambda_i)K_v, \quad (1)$$

wherein $\lambda_i$ (i=1, ... n) denotes the different, defined wavelengths,

I ($\lambda_i$) denotes the intensity of the detected light of the respective wavelength, $I_0$ ($\lambda_i$) denotes the intensity of the light having the respective wavelength that is beamed into the subject or, respectively, the tissue to be examined, d denotes the thickness of the transirradiated tissue region, v (v=1, ... , L) denotes the different tissue components, $K_v$ ($0 \leq K_v \leq 1$) denotes the relative concentration of the respective tissue components, $\alpha_v$ ($\lambda_i$) denotes the extinction coefficient of the respective tissue component at the wavelength $\lambda_i$ and A ($\lambda_i$) denotes the absorption of the tissue under examination at the respective wavelength $\lambda_i$.

In order to be able to examine a larger tissue region, scanning means are provided according to a preferred embodiment that effect a displacement of the light exit zone for conducting a scanning motion. In this case, the evaluation means calculate the relative concentration of the different tissue components as a function of the position of the light exit zone, using the equation $$A(\lambda_i, x_k) = -\log\frac{I(\lambda_i, x_k)}{I_o(\lambda_i)} = d \cdot \sum_{v=1}^{L} \alpha_v(\lambda_i)K_v(x_k), \quad (2)$$

wherein identical symbols have the same meaning as in the case of equation (1), and wherein $x_k$ (k=1, ... , M) denotes the respective position of the light exit zone during the scan motion, I ($\lambda_i$, $x_k$) denotes the intensity of the detected light of the respective wavelength for the respective position of the light exit zone, and $K_v$ ($x_k$) denotes the relative concentration of the respective tissue components for the respective position of the light exit zone.

When the evaluation means operate using equation (1) or equation (2), it is assumed that the intensities $I_0$ ($\lambda_i$) are known and are chronologically constant. This makes high demands on the precision of corresponding calibration measurements, the constancy of the light sources of the means for irradiation, as well as on the stability of the optical infeed or outfeed of the light into and out of the tissue under examination. In order to make these demands less critical, in a preferred and advantageous embodiment of the invention for the case wherein a scan motion occurs, the evaluation means for the different tissue components calculate the change of the relative concentration between successive positions of the light entry zone, employing the equation $$\Delta A(\lambda_i, k) = -\log \frac{I(\lambda_i, x_{k+1})}{I(\lambda_i, x_k)} = d \cdot \sum_{v=1}^{L} \alpha_v(\lambda_i) \Delta K_v(k), \quad (3)$$

wherein identical symbols have the same meaning as in the case of equations (1) and (2) and wherein $\Delta K_v(k)$ corresponds to the change of the relative concentration occurring between the successive positions k and k+1 of the light exit zone for the respective tissue components.

According to one version of the invention, the signals of the detector means are supplied to a logarithmic converter, i.e., a unit such as an amplifier or diode whose output is a logarithmic function of its input. As a result, a simplification of the evaluation means or a reduction of the calculating outlay to be carried out by the evaluation means is achieved, since the changes in absorption occurring between two successive positions of the light exit zone—the positions of the light exit zone shall be referred to below as scanning positions—can be calculated by simple subtraction of the intensities belonging to the neighboring scan positions.

In another embodiment of the invention at least one of the defined, different wavelengths is selected such that it corresponds to the wavelength of an isosbestic point of two of the tissue components. Since the two tissue components have the same extinction coefficient at the isosbestic point, the absorption at the corresponding wavelength is dependent on the ratio of the two tissue components relative to one another. This represents a facilitation in the solution of the linear equation systems described by equation (1) through (3) solved by the evaluation means for calculating the concentrations or concentration changes. The evaluation means thereby operate, for example, according to the method of matrix inversion or method of least square fit.

DESCRIPTION OF THE PREFERRED EMBODIMENTS

Figure 1:
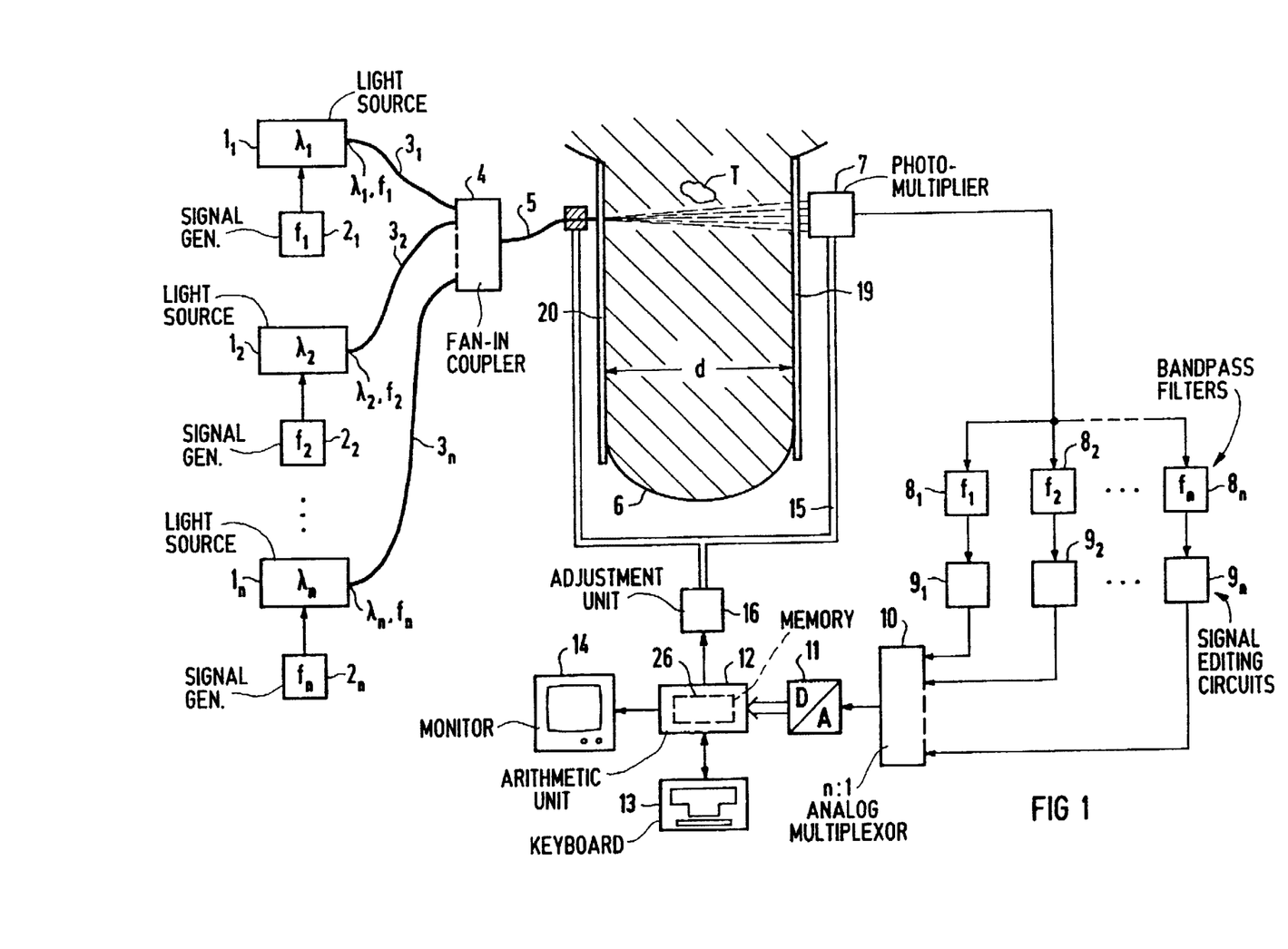
FIG. 1 is a schematic illustration and block circuit diagram of an apparatus constructed and operating in accordance with the principles of the invention.
Figure 2:
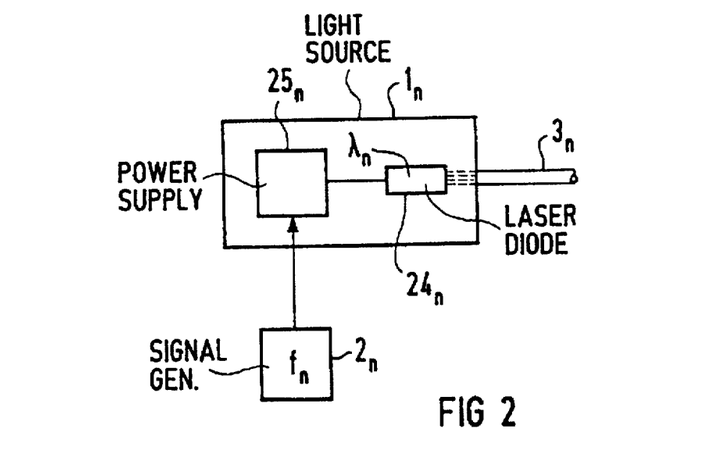
FIG. 2 shows a detail of the apparatus of FIG. 1.

FIG. 1 shows an apparatus of the invention that, for example, can be employed for mammadiagnostics. The apparatus has a plurality of monochromatic light sources $1_1-1_n$, each emitting coherent light at a respectively different wavelength $\lambda_1-\lambda_n$. Each of the light sources $1_1-1_n$ contains a semiconductor laser diode and an associated power supply. This is shown in FIG. 2 which shows the light source $1_n$ with the semiconductor laser diode $24_n$ and the power supply $25_n$. Each light source $1_1-1_n$ has an electrical signal generator $2_1-2_n$ allocated to it that supplies an alternating current signal having a fixed frequency to the power supply contained in the respective light source $1_1-1_n$, the supply current for the semiconductor laser diode contained in the respective light source $1_1-1_n$ being modulated with this alternating current signal. Each of the signal generators $2_1-2_n$ generates an alternating current signal having a different frequency $f_1-f_n$. Since the amplitude or the intensity of the light emitted by the laser diodes is essentially proportional to the intensity of the current from its supply, the light sources $1_1-1_n$ thus emit light having respectively different wavelengths $\lambda_1-\lambda_n$, the light from the sources $1_1-1_n$ being amplitude-modulated with respectively different modulation frequencies $f_1-f_n$. The light emit by the light sources $1_1-1_n$ is supplied via respective light wave guides $3_1-3_n$ to a light wave guide fan-in coupler 4 that comprises has n inputs—each connected to one of the light wave guides $3_1-3_n$—and one output to which a light wave guide 5 is connected. A measuring light signal is supplied via the light wave guide 5, whose free end represents the light exit zone of the apparatus, to a living subject 6 to be examined, namely a body region of a human patient and, in particular, to a breast.

The measuring light signal is generated by superimposition of the light respectively emitted by the light sources $1_1-1_n$ in the light wave guide fan-in coupler 4. The light of the light sources $1_1-1_n$ is supplied to the subject 6 simultaneously and at the same location. It is sufficient, however, if the light of the light sources $1_1-1_n$ is supplied substantially simultaneously (quasi-simultaneously) to the subject. This means that the light from the respective light sources $1_1-1_n$ is emitted in such rapid source-to-source succession that no modifications of the transirradiated tissue can occur between emissions which could lead to an influencing of the measured results. It is also sufficient if the light of the light sources $1_1-1_n$ is supplied to the subject 6 at substantially the same location. For example, it is thus possible to forgo the light wave guide fan-in coupler 4 and instead to employ an optical fiber bundle having one end forming the light exit zone and that is fanned at its other end so that an identical number of optical fibers leads to each of the light sources $1_1-1_n$.

The light exit zone of the apparatus should be located optimally close the surface of the subject 6. Means for detection including a photomultiplier 7 are arranged opposite the light exit zone at that side of the subject 6 facing away from the light exit zone. This means for detection forms the light entry zone of the apparatus into which enters that transmitted part of the measured light signal emerging from the subject 6 lying opposite the light exit zone. The photomultiplier 7 converts the transmitted part of the measured light signal into an electrical signal whose chronological curve represents the chronological curve of the intensity of the received light insofar as it corresponds to the amplitude envelope of the received light. The light entry zone is also arranged close to the surface of the subject 6, that is accepted between compression plates 19 and 20 that are essentially transparent for the measured light signal and proceed planar and parallel to one another. The subject 6 is accepted therebetween such that the subject 6 has an essentially constant thickness d.

The light exit zone and the light entry zone are arranged relative to one another so that the light emanating from the light exit zone is centrally incident into the light entry zone given the absence of a subject 6.

The electrical signal of the photomultiplier 7 is supplied to one of a plurality of band-pass filters $8_1-8_n$, corresponding in number to the plurality of light sources $1_1-1_n$. The bandpass filters $8_1-8_n$ have respective center frequencies $f_1-f_n$ corresponding as exactly as possible to the modulation frequencies $f_1-f_n$. Electrical signals are thus available at the outputs of the bandpass filters $8_1-8_n$ that represent the intensity of the parts of the light having the wavelengths $\lambda_1-\lambda_n$ arising from the light sources $1_1-1_n$ in the detected part of the measured light signal which was transmitted by the subject 6.

The photomultiplier 7 and the band-pass filters $8_1-8_n$ thus form means for detection. Their output signals of the band-pass filter $8_1-8_n$ respectively proceed to signal editing circuits $9_1-9_n$ wherein a signal editing matched to the respective examination ensues, for example by rectification, smoothing or integration. The output signals of the signal editing circuits $9_1-9_n$ are supplied to an n:1 analog multiplexor 10 whose output is connected to the input of an analog-to-digital converter 11. The digital output data of the analog-to-digital converter 11 proceed to evaluation means in the form of an electronic arithmetic unit 12, to which a keyboard 13 for operating the apparatus and a display means in the form of a monitor 14 are connected.

Figure 3:
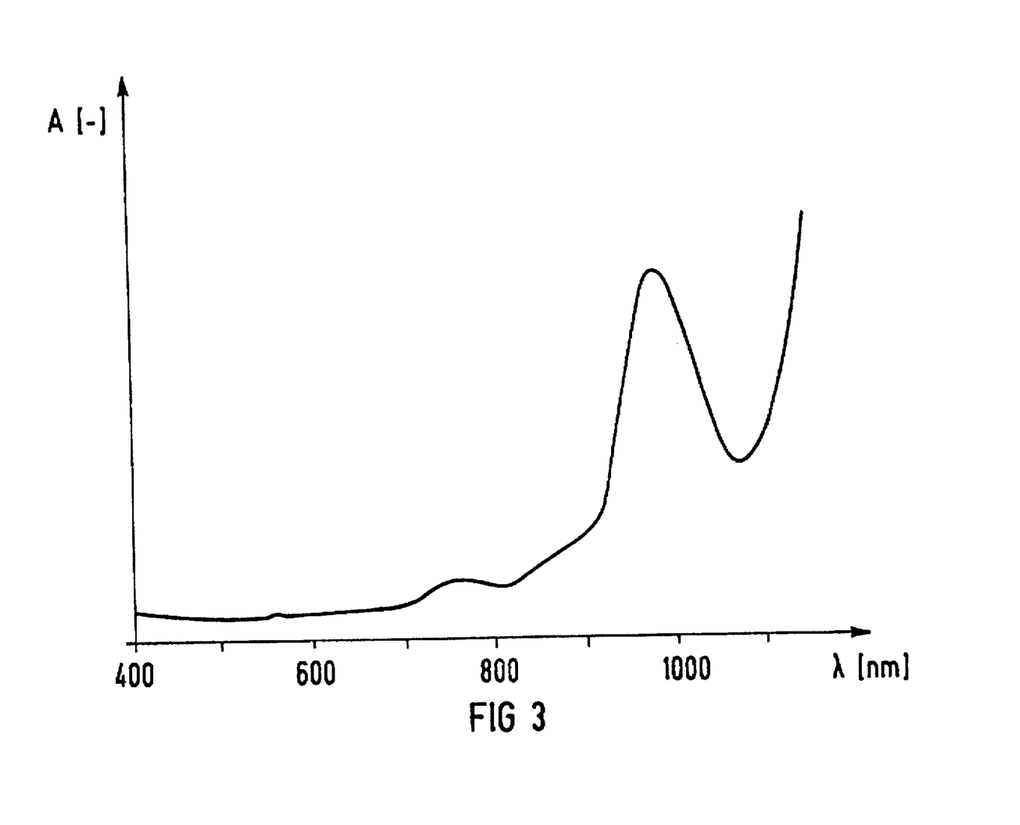
FIGS. 3 and 4 are respectively qualitative illustrations of the absorption spectra of water and female mammary gland tissue.
Figure 4:
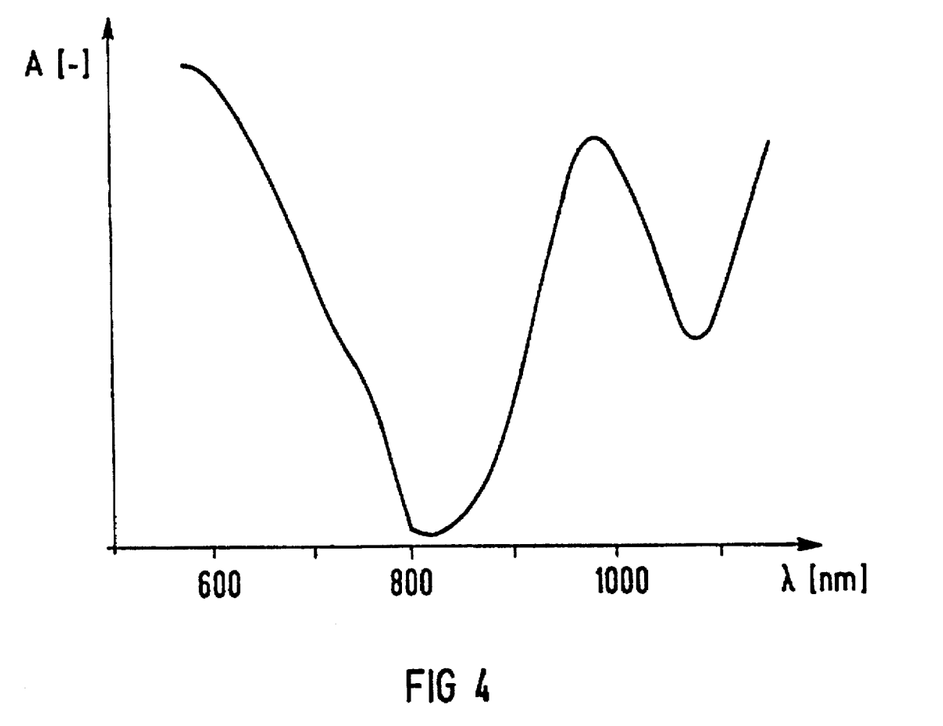

The electronic arithmetic unit 12 contains a memory 26 indicated with broken lines in FIG. 1 wherein data are stored corresponding to the absorption for a plurality of different tissue components, for example muscle tissue, mammary gland tissue, etc. (water, blood and fat should also be considered tissue components in the present case) for the different wavelengths $\lambda_1-\lambda_n$. For example, the respective extinction coefficients $\alpha_v(\lambda_i)$ can be stored in the memory 26. The absorption spectra (absorption A over the wavelength $\lambda$) are schematically shown in FIGS. 3 and 4 for water and female mammary gland tissue. The storing of the data in the memory 26 can, for example, ensue in the form of a function table. The number of different tissue components is selected at most equal to the number of different wavelengths $\lambda_1-\lambda_n$.

Using the data stored in the memory 26, the electronic arithmetic unit 12 calculates data with respect to the concentration, particularly with respect to the relative concentration, of those tissue components in the tissue under examination, the calculated data also being stored in the memory 26.

Figure 5:
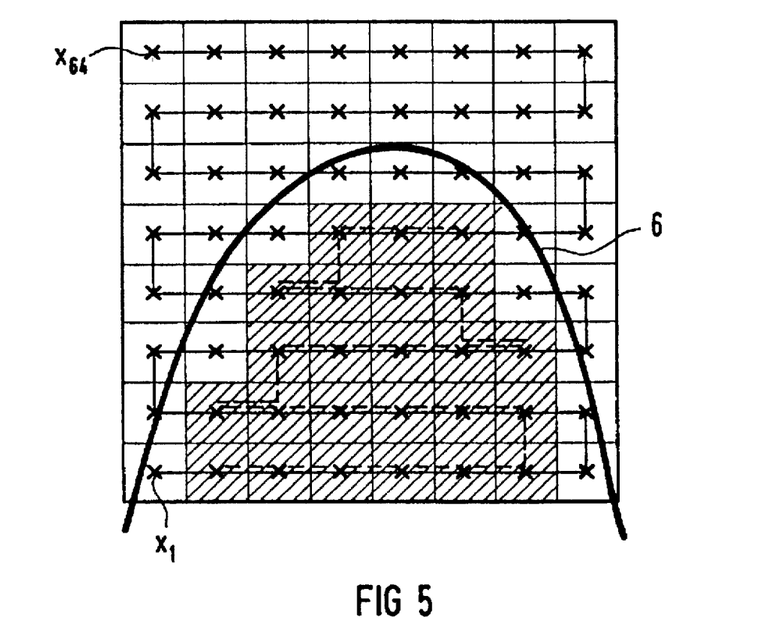
FIG. 5 is a schematic illustration of the scan motion of the apparatus according to FIGS. 1 and 2.

In order to be able to collect data with respect to larger regions of the subject 6, scan means in the form of a carrier 15 for the light wave guide 5 and the photomultiplier 7 are provided. The carrier 15 can be adjusted by an adjustment unit 16 that is controlled by the electronic arithmetic unit 12 so that the light exit zone (and, thus the location of irradiation) and the light entry zone of the apparatus are adjusted relative to the subject 6 in the fashion of a scan motion. The scan motion preferably does not ensue continuously, but instead ensues in such a way that a plurality of discrete scan positions are scanned in succession. For example, it can be provided that data for 256 scan positions are collected during the course of the scan motion, these scan positions being arranged matrix-like in sixteen rows and columns and that have the same spacing from one another both in the row as well as in the column direction (i.e., a grid). The scan motion thereby preferably ensues step-by-step in the form of a serpentine-like motion, as schematically indicated in FIG. 5 for sixty-four scan positions $x_1-x_{64}$ marked by crosses.

The manner by which the electronic arithmetic unit 12 calculates the data with respect to the concentration of the different tissue components is dependent on which of three operating modes of the apparatus is selected with the keyboard 13.

In a first operating mode, the calculation of data ensues only for a signal scan position that, corresponding to the requirements of the current examination case, can be approached by suitable actuation of the keyboard 13.

In this first operating mode, the electronic arithmetic unit 12 calculates the relative concentration of the different tissue components using the equation $$A(\lambda_i) = -\log \frac{I(\lambda_i)}{I_o(\lambda_i)} = d \cdot \sum_{v=1}^{L} \alpha_v(\lambda_i) K_v, \tag{1}$$

wherein $\lambda_i$ (i = 1, ... n) denotes the different, defined wavelengths,

I ($\lambda_i$) denotes the intensity of the detected light of the respective wavelength, $I_o$ ($\lambda_i$) denotes the intensity of the light having the respective wavelength that is beamed into the subject or, respectively, the tissue to be examined, d denotes the thickness of the transirradiated tissue region.

v (v=1, ... , L) denotes the different tissue components, $K_v$ ($0 \leq K_v \leq 1$) denotes the relative concentration of the respective tissue components, $\alpha_v$ ($\lambda_i$) denotes the extinction coefficient of the respective tissue component at the wavelength $\lambda_i$ and A ($\lambda_i$) denotes the absorption of the tissue under examination at the respective wavelength $\lambda_i$.

The data acquired in this way with respect to the relative concentration of the different tissue components are displayed, preferably numerically, on the monitor 14.

In a second operating mode, the above-described scan motion is implemented. From the data thereby collected, the electronic arithmetic unit 12 calculates the concentrations of the different tissue components for the individual scan positions $x_1-x_k$ using the equation $$A(\lambda_i, x_k) = -\log \frac{I(\lambda_i, x_k)}{I_o(\lambda_i)} = d \cdot \sum_{v=1}^{L} \alpha_v(\lambda_i) K_v(x_k), \tag{2}$$

wherein identical symbols have the same meaning as in the case of equation (1), and wherein $x_k$ (k=1, ... , M) denotes the respective position of the light exit zone during the scan motion, I ($\lambda_i$, $x_k$) denotes the intensity of the detected light of the respective wavelength for the respective position of the light exit zone, and $K_v$ ($x_k$) denotes the relative concentration of the respective tissue components for the respective position of the light exit zone.

The data calculated in this way with respect to the relative concentration of the different tissue components are displayed, preferably graphically, on the monitor 14. For example, this can ensue in such a way that different colors are allocated to different tissue components and different brightnesses of a particular color are allocated to different relative concentrations, and the graphic presentation of the arrangement of the relative concentrations corresponds to the arrangement of the scan positions. A graphic display of the relative concentrations for a plurality of tissue components can ensue simultaneously in this way, whereby a plurality of "images" are simultaneously displayed on the monitor 14. The relative concentrations with respect to only one of the different tissue components can alternatively be displayed. Only a single, larger "image" is then displayed on the monitor 14. On the basis of images acquired in this way, there is the possibility of recognizing the presence of inhomogeneities, for example of a tumor T, and of localizing the inhomogeneities.

In a third operating mode, the electronic arithmetic unit 12 does not calculate the relative concentrations of the different tissue components for the individual scan positions, but instead calculates the changes in relative concentration for the different tissue components that occur between successive, and thus neighboring, scan positions. This occurs using the equation $$\Delta A(\lambda_i, k) = -\log \frac{I(\lambda_i, x_{k+1})}{I(\lambda_i, x_k)} = d \cdot \sum_{v=1}^{L} \alpha_v(\lambda_i) \Delta K_v(k), \quad (3)$$

wherein identical symbols have the same meaning as in the case of equations (1) and (2) and wherein $\Delta K_v(k)$ corresponds to the change of the relative concentration occurring between the successive positions k and k+1 of the light exit zone for the respective tissue components.

The presentation of the data calculated in this way on the monitor 14 ensues as set forth above in conjunction with the second operating mode, with the difference that instead of different relative concentrations, changes of the relative concentration have different brightness values allocated to them.

Figure 6:
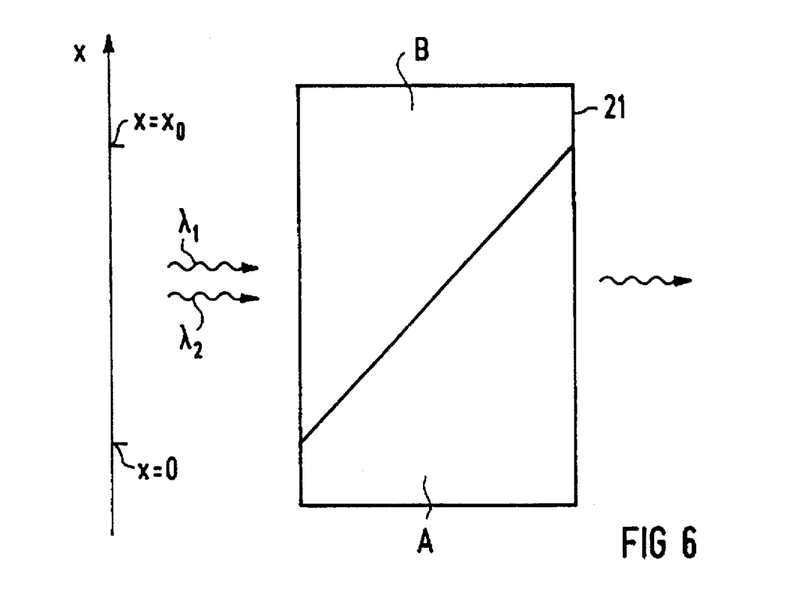
FIG. 6 is a diagram for explaining the functioning of the apparatus according to FIGS. 1 and 2.

A simple model example shown in FIG. 6 is intended to illustrate the interrelationships on which the functioning of the apparatus of the invention are based.

Let a model member 21 of constant thickness composed of two tissue components A and B be assumed, so that a transirradiation with light having two wavelengths $\lambda_1$ and, respectively, $\lambda_2$ is adequate for calculating the changes of the relative concentration between neighboring scan positions.

Tissue component A is a tissue component whose extinction is independent of wavelength. Thus $\alpha_A(\lambda_1) = \alpha_A(\lambda_2) = \alpha$ is valid.

The wavelength $\lambda_1$ is selected such that it corresponds to the wavelength of the isosbestic point. The following is thus valid:

$$\alpha_A(\lambda_1) = \alpha_B(\lambda_1) = \alpha$$

Let the extinction coefficient of the tissue component B for the wavelength $\lambda_2$ be $\alpha_B(\lambda_2) = \alpha + \beta\alpha$.

As shown in FIG. 6, the model member 21 is of such a nature that the relative concentration of the tissue component A decreases linearly in the x-direction, whereas that of the tissue component B increases linearly in that direction.

When the model member 21 is scanned by a scan motion proceeding in the x-direction, given a transirradiation direction proceeding from left to right transversely relative to the scan motion, then $$\Delta A(v_1, x) = 0,$$

arises for the change in absorption for the first wavelength $\lambda_1$, namely because the wavelength $\lambda_1$ corresponds to the wavelength of an isosbestic point.

The following is valid for a change in absorption with respect to the wavelength $\lambda_2$:

$$\Delta A(\lambda_2, x) = \beta\alpha\Delta x/x_0,$$

i.e. a linear increase or decrease (dependent on the scan direction).

Solving equation (3) for the model example yields $$\Delta K_A = -\Delta K_B$$

and $$\Delta K_A = -\Delta x/x_0 \text{ or, respectively, } \Delta K_B = \Delta x/x_0,$$

i.e. a linear increase of the component B or a linear decrease of the component A.

The following is thus valid for the curves of the relative concentration:

$$K_A = a - x/x_0 \text{ or, respectively, } K_B = b + x/x_0,$$

the values of the additive constants a or b not being able to be determined by solving equation (3).

The determination of these constants, however, would be possible if the absorptions for the individual scan positions were measured instead of the changes in absorption between neighboring scan positions. In this case, the constants a and b would also be determined during the course of solving equation (2).

Figure 7:
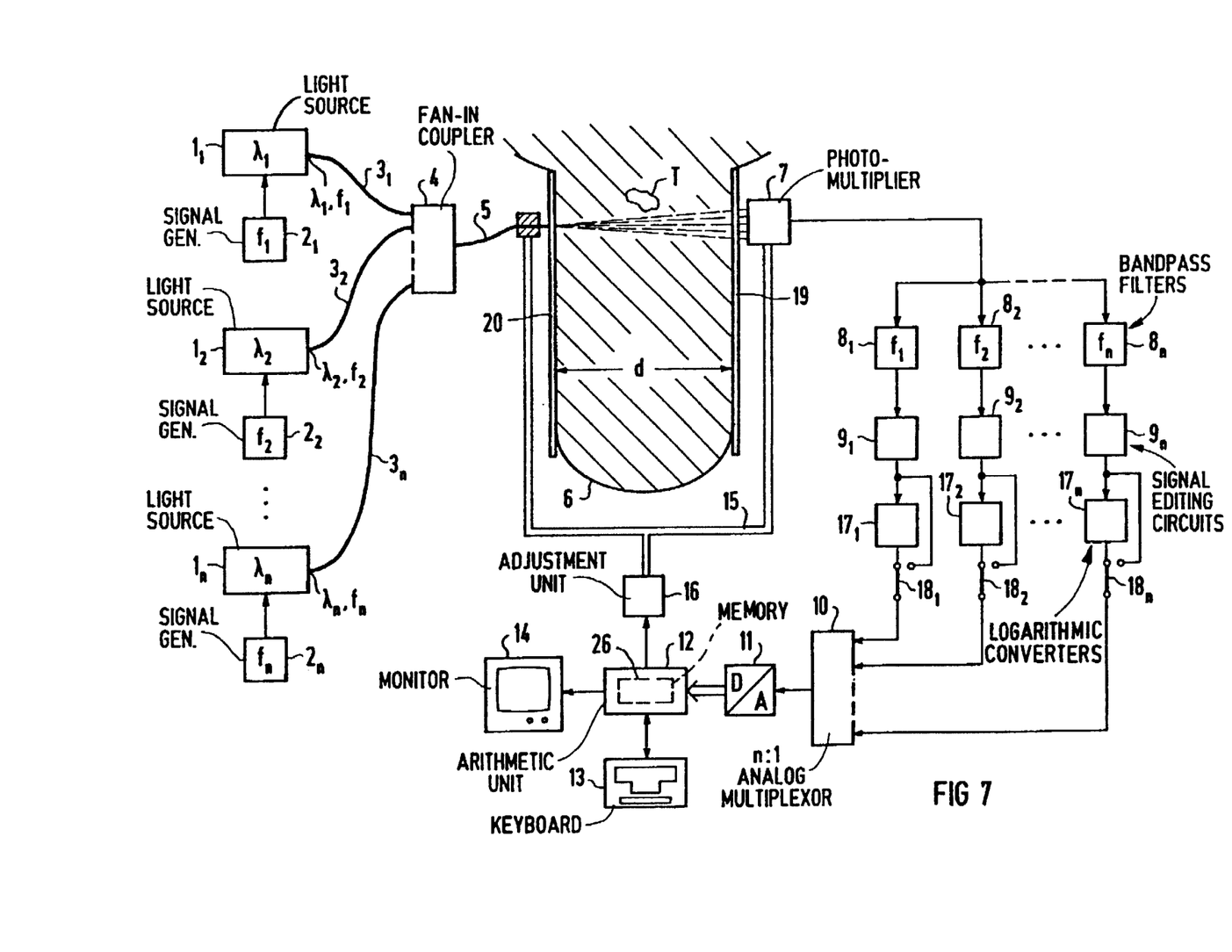
FIG. 7 shows a modification of the apparatus according to FIGS. 1 and 2.

FIG. 7 shows a further exemplary embodiment of the invention. It initially differs from the embodiment set forth above in that at least one of the wavelengths $\lambda_1-\lambda_n$ is selected such that it corresponds to the wavelength of the isosbestic point of two of the tissue components with respect to which data are stored in the memory 26. In this case, since changes of the relationship of the corresponding tissue components relative to one another do not influence the measured absorption or the measured changes in absorption, a reduced calculating outlay results for the electronic arithmetic unit 12.

A further difference is that logarithmic converters $17_1-17_n$ are connected between the signal editing circuits $9_1-9_n$ and the multiplexor 10. Further, switches $18_1-18_n$ are provided that allow the logarithmic converters $17_1-17_n$ to be bypassed.

When the apparatus of FIG. 7 operates in the first, second or third mode set forth in conjunction with the above-described exemplary embodiment, the electronic arithmetic unit 12 actuates the switches $18_1-18_n$ such that the logarithmic converters $17_1-17_n$ are bypassed. The apparatus according to FIG. 7 then does not differ in function with respect to the three operating modes already set forth when compared to the above-described apparatus. The apparatus of FIG. 7, however, can be operated in a fourth operating mode, corresponding to the third operating mode but with the difference that the switches $18_1-18_n$ are actuated by the electronic arithmetic unit 12 such that the logarithmic converters $17_1-17_n$ lie in the signal path. The change in absorption between two neighboring scan points can then easily be identified by subtracting the corresponding logarithmized signals, so that the calculating outlay to be performed by the electronic arithmetic unit 12 is reduced further.

In the described exemplary embodiments, the photomultiplier 7 is arranged such that it directly picks up the light emerging from the subject 6. There is also the possibility of picking up the light emerging from the subject 6 with a fiber-optical light wave guide or light wave guide bundle attached to the carrier 15 instead of the photomultiplier 7 supplying the light this to the photomultiplier 7.

The means for detection can alternatively include a photodiode or a CCD instead of the photomultiplier 7.

An LED, LCD or plasma display can alternatively be provided as display means instead of the monitor 14.

The means for emitting light into the subject set forth in conjunction with the exemplary embodiments, formed by the light sources $1_1-1_n$, the signal generators $2_1-2_n$, the light wave guides $3_1-3_n$, the light wave guide fan-in coupler 4 and the light wave guide 5 in the case of the exemplary embodiments, can also be differently fashioned. For example, the simultaneous infeed of the light of the light sources $1_1-1_n$ at the same location can also be effected with a mirror arrangement.

The fashioning of the scan means described herein is also only as an example. A different structure of the scan means as well as scan motions deviating from the scan motion that has been set forth are possible.

In the exemplary embodiments that have been set forth, the subject to be examined is arranged between the two compression plates 19 and 20, so that an essentially constant thickness of the subject 6 results. If such a compression of the subject under examination should not prove possible, there is also the possibility of mensurationally acquiring a variable thickness d of the subject and supplying the arithmetic unit 12 with corresponding signals. A person skilled in the art can undertake appropriate measures without undue experimentation.

The data stored in the memory 26 can be acquired by measurements of specimens in vitro. For example, an exclusively fatty tissue spectrum, an exclusively mammary gland tissue spectrum, an exclusively blood spectrum, etc., can be registered.

When the apparatus is fashioned such that it operates only in an operating mode corresponding to the above-described, fourth operating mode, a simplified structure of the electronic arithmetic unit 12 is possible, since this need not execute any logarithmizing operations in the evaluation of the data supplied to it.

In order to avoid overexposure of the photomultiplier 7 by direct irradiation with the measuring light signal, there is the possibility of controlling the serpentine-like scan motion using a suitable sensor that, as indicated with broken lines in FIG. 5, acquires only those scan positions wherein it is assured that the subject 6 is located between the light exit zone and light entry zone. These scan positions are shaded in FIG. 5.

Although modifications and changes may be suggested by those skilled in the art, it is the intention of the inventors to embody within the patent warranted hereon all changes and modifications as reasonably and properly come within the scope of their contribution to the art.

We claim as our invention:

1. An apparatus for examining blood and substantially stationary tissue by transillumination of said blood and substantially stationary tissue with light, comprising:

means for conducting an examination of blood and substantially stationary tissue including a plurality of monochromatic light sources respectively emitting light at defined, different wavelengths into said blood and substantially stationary tissue substantially simultaneously from a light entry zone which is substantially the same for the light of each wavelength, said light passing through said blood and substantially stationary tissue and emerging from said blood and substantially stationary tissue at a light exit zone with light from the different light sources having respective intensities at said different wavelengths;

means for receiving said light to obtain detected light after passing through the blood and substantially stationary tissue, having a light reception zone disposed opposite said light exit zone, and for producing output signals corresponding to the respective intensities in substantially all of the detected light of the parts of the detected light having said defined, different wavelengths; and evaluation means, supplied with said output signals of said means for receiving said light, for identifying the concentration of a plurality of different blood and tissue components in said blood and stationary tissue, said evaluation means including a memory containing stored data corresponding to absorption by different blood and tissue components, obtained prior to said examination, for each of said different blood and tissue components respectively corresponding to the absorption of light at said defined, different wavelengths by the respective blood and tissue components, and said evaluation means identifying said concentration of a number of said different blood and tissue components corresponding at most in number to the plurality of defined, different wavelengths from said output signals and said stored data.

2. An apparatus as claimed in claim 1 wherein said evaluation means comprises means for identifying a relative concentration of said different tissue components according to the relationship $$A(\lambda_i) = -\log \frac{I(\lambda_i)}{I_o(\lambda_i)} = d \cdot \sum_{v=1}^{L} \alpha_v(\lambda_i) K_v$$

wherein $\lambda_i$ (i=1,... n) denotes the different, defined wavelengths, $I(\lambda_i)$ denotes the intensity of the detected light of the respective wavelengths $\lambda_i$, $I_o(\lambda_i)$ denotes the intensity of the light having the respective wavelength $\lambda_i$ that is emitted into the tissue to be examined, d denotes the thickness of the transilluminated tissue region, v (v=1,..., L) denotes the different tissue components, $K_v$ ($0 \leq K_v \leq 1$) denotes the relative concentration of the respective tissue components, $\alpha_v(\lambda_i)$ denotes the extinction coefficient of the respective tissue component at the wavelength $\lambda_i$ and $A(\lambda_i)$ denotes the absorption of the tissue under examination at the respective wavelength $\lambda_i$.

3. An apparatus as claimed in claim 1 further comprising scan means connected to said light entry zone for effecting displacement of said light entry zone in a scan motion around said tissue.

4. An apparatus as claimed in claim 3 wherein said evaluation means comprises means for identifying the relative concentration of said different components as a function of a position of said light exit zone in said scan motion, according to the relationship $$A(\lambda_i, x_k) = -\log \frac{I(\lambda_i, x_k)}{I_o(\lambda_i)} = d \cdot \sum_{v=1}^{L} \alpha_v(\lambda_i) K_v(x_k)$$

wherein $\lambda_i$ (i=1,... n) denotes the different, defined wavelengths, $x_k$ (k=1,..., M) denotes the respective position of the light exit zone during the scan motion, $I(\lambda_i, x_k)$ denotes the intensity of the detected light of the respective wavelength $\lambda_i$ for the respective position $X_k$ of the light exit zone, $I_o(\lambda_i)$ denotes the intensity of the light having the respective wavelength that is emitted into the tissue to be examined, d denotes the thickness of the transilluminated tissue region, v (v=1,..., L) denotes the different tissue components, $\alpha_v(\lambda_i)$ denotes the extinction coefficient of the respective tissue component at the wavelength $\lambda_i$, $K_v(x_k)$ denotes the relative concentration of the respective tissue component for the respective position of the light exit zone, and $A(\lambda_i)$ denotes the absorption of the tissue under examination at the respective wavelength $\lambda_i$.

5. An apparatus as claimed in claim 3 wherein said evaluation means comprises means for calculating a change in said relative concentration of said different tissue components between successive positions of said light exit zone in said scan motion, according to the relationship $$\Delta A(\lambda_i, k) = -\log \frac{I(\lambda_i, x_{k+1})}{I(\lambda_i, x_k)} = d \cdot \sum_{v=1}^{L} \alpha_v(\lambda_i) \Delta K_v(k)$$

wherein $\lambda_i$ (i=1, ... n) denotes the different, defined wavelengths, $x_k$ (k=1, ... , M) denotes the respective position of the light exit zone during the scan motion, I $(\lambda_i, x_k)$ denotes the intensity of the detected light of the respective wavelength $\lambda_i$ for the respective position $x_k$ of the light exit zone, $I_0$ $(\lambda_i)$ denotes the intensity of the light having the respective wavelength that is emitted into the tissue to be examined, d denotes the thickness of the transilluminated tissue region, v (v=1, ... , L) denotes the different tissue components, $\alpha_v$ $(\lambda_i)$ denotes the extinction coefficient of the respective tissue component at the wavelength $\lambda_i$, $\Delta K_v(k)$ denotes the change of the relative concentration occurring between the positions k and k+1 of the light exit zone, and $\Delta A$ $(\lambda_i)$ denotes the change in absorption of the tissue under examination between the positions k and k+1 of the light exit zone at the respective wavelength $\lambda_i$.

6. An apparatus as claimed in claim 3 further comprising means in said receiver means for logarithmically converting said output signals before said output signals are supplied to said evaluation means.

7. An apparatus as claimed in claim 1 wherein two of said tissue components have an isosbestic point having a wavelength associated therewith, and wherein said plurality of monochromatic light sources includes at least one monochromatic light source emitting light at a defined wavelength corresponding to said wavelength associated with said isosbestic point.

8. A method for examining blood and substantially stationary tissue by transillumination of said blood and substantially stationary tissue with light, comprising:

conducting an examination of blood and substantially stationary tissue by emitting light from a plurality of monochromatic light sources having respective defined, different wavelengths into said blood and substantially stationary tissue substantially simultaneously from a light entry zone which is substantially the same for the light of each wavelength, said light passing through said blood and substantially stationary tissue and emerging from said blood and substantially stationary tissue at a light exit zone with light from the different light sources having respective intensities at said different wavelengths;

receiving said light from said light exit zone to obtain detected light and producing output signals corresponding to the respective intensities in substantially all of the detected light of the parts of the detected light having said defined, different wavelengths;

storing data corresponding to absorption by different blood and tissue components, obtained prior to said examination, for each of a plurality of blood and tissue components of said blood and stationary tissues corresponding to an absorption of light at said defined, different wavelengths by respective blood and tissue components; and identifying the concentration of a number of said different blood and tissue components corresponding at most in number to the plurality of defined, different wavelengths from said output signals and said stored data.

9. A method as claimed in claim 8 wherein the step of identifying the concentration comprises identifying a relative concentration of said different tissue components according to the relationship $$A(\lambda_i) = -\log \frac{I(\lambda_i)}{I_o(\lambda_i)} = d \cdot \sum_{v=1}^{L} \alpha_v(\lambda_i) K_v$$

wherein $\lambda_i$ (i=1, ... n) denotes the different, defined wavelengths,

I $(\lambda_i)$ denotes the intensity of the detected light of the respective wavelengths $\lambda_i$, $I_0$ $(\lambda_i)$ denotes the intensity of the light having the respective wavelength $\lambda_i$ that is emitted into the tissue to be examined, d denotes the thickness of the transilluminated tissue region, v (v=1, ... , L) denotes the different tissue components, $K_v$ $(0 \leq K_v \leq 1)$ denotes the relative concentration of the respective tissue components, $\alpha_v$ $(\lambda_i)$ denotes the extinction coefficient of the respective tissue component at the wavelength $\lambda_i$ and A $(\lambda_i)$ denotes the absorption of the tissue under examination at the respective wavelength $\lambda_i$.

10. A method as claimed in claim 8 comprising the additional steps of effecting displacement of said light entry zone in a scan motion around said tissue.

11. A method as claimed in claim 10 wherein the step of identifying the concentration comprises identifying the relative concentration of said different components as a function of the position of said light exit zone in said scan motion, according to the relationship $$A(\lambda_i, x_k) = -\log \frac{I(\lambda_i, x_k)}{I_o(\lambda_i)} = d \cdot \sum_{v=1}^{L} \alpha_v(\lambda_i) K_v(x_k)$$

wherein $\lambda_i$ (i=1, ... n) denotes the different, defined wavelengths, $x_k$ (k=1, ... , M) denotes the respective position of the light exit zone during the scan motion, I $(\lambda_i, x_k)$ denotes the intensity of the detected light of the respective wavelength $\lambda_i$ for the respective position $x_k$ of the light exit zone, $I_0$ $(\lambda_i)$ denotes the intensity of the light having the respective wavelength that is emitted into the tissue to be examined, d denotes the thickness of the transilluminated tissue region, v (v=1, ... , L) denotes the different tissue components, $\alpha_v$ $(\lambda_i)$ denotes the extinction coefficient of the respective tissue component at the wavelength $\lambda_i$, $K_v$ $(x_k)$ denotes the relative concentration of the respective tissue component for the respective position of the light exit zone, and A $(\lambda_i)$ denotes the absorption of the tissue under examination at the respective wavelength $\lambda_i$.

12. A method as claimed in claim 10 wherein the steps of identifying the concentration comprises calculating a change in said relative concentration of said different tissue components between successive positions of said light exit zone in said scan motion, according to the relationship $$\Delta A(\lambda_i, k) = -\log \frac{I(\lambda_i, x_{k+1})}{I(\lambda_i, x_k)} = d \cdot \sum_{v=1}^{L} \alpha_v(\lambda_i) \Delta K_v(k)$$

wherein $\lambda_i$ (i=1, ... n) denotes the different, defined wavelengths, $x_k$ (k=1, ... , M) denotes the respective position of the light exit zone during the scan motion, $I(\lambda_i, x_k)$ denotes the intensity of the detected light of the respective wavelength $\lambda_i$ for the respective position $x_k$ of the light exit zone, $I_0(\lambda_i)$ denotes the intensity of the light having the respective wavelength that is emitted into the tissue to be examined, d denotes the thickness of the transilluminated tissue region, v (v=1, ... , L) denotes the different tissue components, $\alpha_v(\lambda_i)$ denotes the extinction coefficient of the respective tissue component at the wavelength $\lambda_i$, $\Delta K_v(k)$ denotes the change of the relative concentration occurring between the positions k and k+1 of the light exit zone, and $\Delta A(\lambda_i)$ denotes the change in absorption of the tissue under examination between the positions k and k+1 of the light exit zone at the respective wavelength $\lambda_i$.

13. A method as claimed in claim 8 comprising the additional step of logarithmically converting said output signals before said output signals are used to identify said concentration.

14. A method as claimed in claim 8 wherein two of said tissue components have an isosbestic point having a wavelength associated therewith, and wherein the step of emitting light comprises emitting light from at least one monochromatic light source at a defined wavelength corresponding to said wavelength associated with said isosbestic point.

* * * * *